United States Patent [19]

Toro et al.

[11] Patent Number: 5,241,063

[45] Date of Patent: Aug. 31, 1993

[54] PROCESS FOR THE PREPARATION OF STEROIDS BEARING 17α-HYDROXY-20-OXOPREGNANE SIDE CHAIN

[75] Inventors: Andras Toro; Gabor Ambrus; Istvan Pallagi, all of Budapest; Nandor Makk, Kismaros; Gyula Horvath, Budapest; Ferenc Szederkenyi, Budapest; Eva Ilkoy, Budapest; Antonia Jekkel, Budapest; Imre Moravcsik, Budapest; Kalman Könczöl, Budapest, all of Hungary

[73] Assignee: Richter Gedeon Vegyeszeti Gyar Rt., Budapest, Hungary

[21] Appl. No.: 717,823

[22] Filed: Jun. 19, 1991

[30] Foreign Application Priority Data

Jun. 19, 1990 [HU] Hungary .............................. 3896/90

[51] Int. Cl.⁵ .............................................. C07J 21/00
[52] U.S. Cl. ....................................... 540/46; 552/592
[58] Field of Search .................... 540/46; 552/508, 592

[56] References Cited

U.S. PATENT DOCUMENTS 2,249,911  7/1941  Oppenauer et al. .................. 540/46

OTHER PUBLICATIONS

Steroids, L. F. Fieser and Fieser, p. 577 Reinhold Publ. Co., New York, 1959.

Primary Examiner—Marianne M. Cintins
Assistant Examiner—Kimberly J. Kestler
Attorney, Agent, or Firm—Herbert Dubno; Jonathan Myers

[57] ABSTRACT

The invention relates to a novel process for the preparation of 17 α-hydroxy-20-oxopregnane derivatives of the general formula (I),

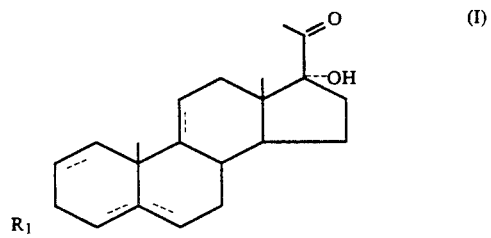

wherein
  $R_1$ means a hydroxy or an oxo group; and
  the dotted lines optionally represent one or more additional valence bond(s), with the proviso that the dotted line in the 4-position and the dotted line in the 5-position cannot each simultaneously be an additional valence bond from steroids having 23,24-dinor-17(20)-dehydrocholan -22-oic acid structure.

According to the process of the invention a steroid derivative having 23,24-dinorcholan-22-oic acid structure, containing a double bond in 17(20)-position, is transformed to 17α, 20-epoxy-23,24-dinorcholanoic acid, the latter is converted to a reactive acid derivative, which is then reacted with a salt-containing azide ion to yield a 17α, 20-epoxy-23,24-dinorcholanoic acyl azide derivative and the azide obtained is reacted with a mineral or organic acid in an aqueous medium.

7 Claims, No Drawings

PROCESS FOR THE PREPARATION OF STEROIDS BEARING 17α-HYDROXY-20-OXOPREGNANE SIDE CHAIN

FIELD OF THE INVNETION

This invention relates to a novel process for the preparation of 17α-hydroxy-20-oxopregnane derivatives of the formula (I),

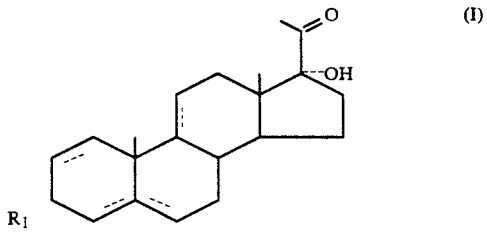

wherein
R₁ stands for hydroxy or oxo group; and
the dotted lines optionally represent one or more additional valence bonds, with the proviso that the dotted line in the 4-positiona and the dotted line in the 5-position cannot each simultaneously be an additional valence bond, from steroids having 23,24-dinor-17(20) -dehydrocholan-22-oic acid structure. The invention also relates to the novel intermediates used in the synthesis of the above compounds of formula (I).

BACKGROUND OF THE INVENTION

In the field of steroids 17α-hydroxy-20-oxopregnane derivatives are utilized as intermediates in the syntheses of the glucocorticoidal hydrocortisone hormone and antiinflammatory corticosteroid drugs (prednisolone, triamcinolone, dexamethasone, betamethasone and the like) developed therefrom, as well as the gestagenic 17α-hydroxyprogesterone-17-ester derivatives (17α-hydroxyprogesterone capronate, chlormadinone acetate and the like) and the antiandrogenic drug cyproterone acetate.

The 17α-hydroxy-20-oxopregnane derivatives used as intermediates in the pharmaceutical industry are prepared on the one hand by transforming 3β-acetoxy-5,16-pregnadien-20-one obtained from the chemical decomposition of diosgenin and of the structurally related solasodine, a steroidal alkaloid [N. Applezweig: Steroid Drugs Vol. 1., page 56, McGraw Hill Corporation, New York, 1962]; and on the other hand, by the synthetic building up of the pregnane side chanin from 17-oxo steroids containing the androstane skeleton [J. Fried and J. A. Edwards: Organic Reactions in Steroid Chemistry, Vol. 2, page 127, van Nostrand Reinhold Company, N.Y., 1972].

It is known that 17(20)-dehydro-23,24-dinorcholanoic acid [U.S. Pat. specification No. 4,132,408], 9α-hydroxy-3-oxo-23,24-dinor-4,17(20)-choladien -22-oic acid [M. G. Wovcha et al.: Biochim. Biophys Acta 531, 308 (1978); published European patent application No. 0,011,235; A. Jekkel et al.: J. Gen. Microbiol. 135, 1727 (1989)] and 3β-hydroxy-23,24-dinor-5,17(20) -choladien-22-oic acid [Hungarian patent specification No. 190,665 (1980)] can be prepared by the partial microbiological decomposition of the side chain of natural sterols.

Natural sterols, particularly those of plant origin, such as the mixture of β-sitosterol and campesterin obtained from soy bean or sterol mixtures obtaned from the side products of wood processing are available in large quantities.

OBJECT OF THE INVENTION

Thus, it is an object of the invention to prepare intermediates containing pregnane skeleton, being useful in the synthesis of drugs, from 17(20)-dehydro-23,24-dinorcholanoic acid derivatives which can economically be obtained by the microbiological decomposition of the above sterol mixtures.

DESCRIPTION OF THE INVENTION

9α-Hydroxy-3-oxo-23,24-dinor -4,17(20)-choladien-22-oic acid is an advantageous starting material particularly for the synthesis of hydrocortisone and the antiinflammatory corticosteroid drugs since it can be transformed to 3-oxo-23,24-dinor-4,9(11),17(20) -cholatrien-22-oic acid by splitting off its 9α-hydroxyl group with chlorosulfonic acid [United Kingdom patent specification No. 2,199,325]; furthermore, the double bond present in 9(11)-position of the latter derivative gives the posssibility to advantageously establish a 11β-hydroxyl group characteristic of corticosteroids, as well as to introduce fluorine or chlorine to 9α-position of the sterane skeleton as substitutents for enhancing the antiinflammatory effect [V. vanRheenen and K. P. Shephard: J. Org. Chem. 44, 1582 (1979); G. R. Allen and M. J. Weiss: J. Am. Chem. Soc. 81, 4968 (1959)].

The double bond in 1,2-position occurring both in the antiinflammatory corticosteroids as well as in gestagenic drugs can also be introduced to 17(20)-dehydro-23,24-dinorcholanoic acids: e.g. 3-oxo-23,24-dinor -4,.9(11),17(20)-cholatrien -22-oic acid can be dehydrogenated to 3-oxo -23,24-dinor-1,4,9(11),17(20) -cholatetraen-22-oic acid in a microbiological way by using Arthrobacter simplex [Hungarian patent specification No. 200,203].

Surprisingly, it has been observed in the course of our investigations that the reaction of 17(20)-dehydro -23,24-dinor-cholanoic acids with hydrogen peroxide in pyridine medium in the presence of a salt of transition metal oxoacids such as ammonium paramolybdate or sodium tungstate selectively leads to 17α, 20-epoxy derivatives so far unknown in the literature. It has been furthermore observed that the acyl azide derivatives prepared from the novel 17α,20-epoxy-23,24-dinorcholanoic acids thus obtained are rearranged under the influence of heat and decomposed to 17α-hydroxy-20-oxopregnane derivatives under the effect of aqueous acids.

Thus, the invention relates to a novel process for the preparation of steroids containing the 17α-hydroxy -20-oxopregnane side chain, which comprises a) reacting a new 17α,20-epoxypregnanyl -20-isocyanate of formula (II)

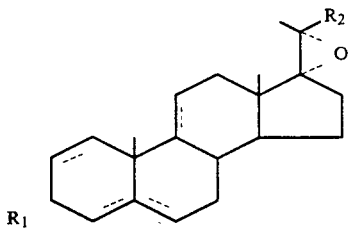

prepared in situ, wherein the meanings of $R_1$ and the dotted lines are as defined above and $R_2$ stands for —NCO group, with a mineral or organic acid in an aqueous organic solvent; or b) reacting a new 17α,20-epoxy-23,24-dinorcholanoly azide of formula (II), wherein the meanings of $R_1$ and the dotted lines are as defined above and $R_2$ stands for —CON$_3$ group, with a mineral or organic acid in an aqueous organic solvent at a temperature above 40° C.; or c) transforming a new 17α,20-epoxy-23,24-dinorcholanoic acid of the formula (II), wherein the meanings of $R_1$ and the dottted lines are as defined above and $R_2$ stands for a carboxyl group, to a reactive derivative, converting the latter to a new 17α,20-epoxy-23,24-dinorcholanoic azide of the formula (II), wherein the meanings of $R_1$ and the dotted lines are as defined above and $R_2$ stands for —CON$_3$ group, by using a salt-containing azide ion and reacting the product obtained with a mineral or organic acid in an aqueous organic solvent at a temperature above 40° C.; or d) reacting a known steroid of the formula (III),

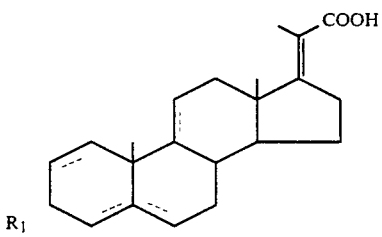

having 23,24-dinor-17(20)-dehydro -cholanoic acid structure, wherein the meanings of $R_1$ and the dotted lines are as defined above, with hydrogen peroxide in an aqueous organic solvent, in the presence of a salt of a transition metal oxoacid or a peroxide derivative thereof or a complex of the peroxide thereof formed with a tertiary amine or an acyl amide as catalyst, then transforming the thus-obtained new 17α,20-epoxy -23,24-dinorcholanoic acid, wherein the meanings of $R_1$ and the dotted lines are as defined above and $R_2$ stands for a carboxyl group, to a reactive derivative, converting the latter to a new 17α,20-epoxy-23,24-dinorcholanoyl azide of the general formula (II), wherein the meanings of $R_1$ and the lines are as defined above and $R_2$ stands for —CON$_3$ group, by using a salt containing azide ion and reacting the product obtained with a mineral or organic acid in an aqueous organic solvent at a temperature above 40° C.

According to a preferred embodiment of the process the invention, the 17(20) double bond conjugated with the carboxyl group in the 17(20)-dehydro -23,24-dinorcholanoic acids used as starting substance for the synthesis is transformed to an α-epoxide by using preferably 30% aqueous hydrogen peroxide at a temperature between 20° C. and 100° C. in the presence of a salt of transition metal oxoacid or a peroxide derivative thereof as catalyst. Suitable catalysts are e.g. sodium tungstate or ammonium paramolybdate. This transformation may preferably be carried out in a nitrogen-containing organic solvent, suitably pyridine, N,N-dimethylformamide, N,N-dimethylacetamide or hexamethylphosphoric acid triamide. It is convenient to form the epoxide at a temperature between 40° C. and 80° C. when using sodium tungstate as catalyst in pyridine medium; or at a temperature between 20° C. and 50° C. when using ammonium paramolybdate as catalyst.

The peroxide derivatives of the salt of transition metal, oxoacids used in the reaction, e.g. the salt containing pertungstate or permolybdate anions, may be prepared either before carrying out the reaction or in situ in the reaction mixture. Sodium pertungstate may be prepared e.g. according to V. A. Lunenok-Burmakina et al. [Zh. Fiz. Khim, 43, 2723 (1969)]. The complexes of pertungstate and permolybdate salts with various nitrogen-containing compounds, e.g. with 8-hydroxyquinoline, α, α-dipyridyl or hexamethylphosphoric acid triamide, may also be utilized as active reagents in the epoxide formation. Such complexes are e.g. $H_2MoO_6 \cdot OP(NMe_2)_3$ (German patent specification No. 1,815,998) and $H_2WO_6 xα,α$-dipyridyl [R. G. Beiles and E. M. Beiles: Zh. Neorg. Khim. 12, 1399 (1967)]. In this case the epoxide-forming reaction is carried out in an aqueous, water-miscible organic sovlent, e.g. tert-butanol.

The 17α,20-epoxy-23,24-dinorcholanoic acid derivatives arising from the reaction can be separated from the reaction mixture by using methods known per se.

The novel 17α,20-epoxy-23,24-dinorcholanoic acids obtained as intermediates in the process according to the invention can be transformed to reactive acid derivatives, preferably mixed anhydrides in a known way: 17α,20-epoxy -23,24-dinorcholanoic acids may be reacted e.g. with methyl, ethyl or isobutyl chloroformate in the presence of a tertiary amine base, preferably triethylamine at a temperature between −20° C. and +20° C. to give mixed acid anhydrides.

In the process according to the invention the intermediate mixed acid anhydride may directly be transformed without isolation to the corresponding acyl azide derivative by using a salt containing azide anion, preferably an alkaline metal azide, suitably sodium azide, at a temperature below 45° C.

According to the invention the intermediate acyl azide may be prepared also by nitrosating 17α,20-epoxy-23,24-dinorcholanoic acyl hydrazide derivatives or by reacting 17α,20-epoxy-23,24-dinorcholanoic acid chlorides with sodium azide.

If desired, the acyl azides occurring as itnermediates in the process according to the invention may be separated from the reaction mixture; however, it is more suitable to react these compounds without isolation.

Under the effect of heat, i.e. on heating above 40° C., the acyl azide intermediate is rearranged to the corresponding isocyanate, which is then decomposed to a steroid derivative containing the 17α-hydroxy-20-oxo-pregnane side chain in $C_{1-5}$ aliphatic alcohol(s) or dimethylformamide on the effect of organic or inorganic acids or reagents providing the above acids under conditions of the reaction, preferably by treatment with aqueous acetic acid.

In the course of the above transformation the intermediate isocyanate can be detected in the reaction mixture by spectroscopical means, however, it cannot be isolated.

The structures of the synthetized products bearing 17α-hydroxy -20-oxopregnane side chain and the structures of intermediates isolated were proven by ultraviolet, infrared, $^1$H-NMR and $^{13}$C-NMR as well as mass spectroscopy.

SPECIFIC EXAMPLES

The process according to the invention is illustrated in detail by the aid of the following non-limiting Examples.

EXAMPLE 1

Preparation of 17α-hydroxy-4-pregnene -3,20-dione from 3-oxo-23,24-dinor 4,17(20)-choladien-22-oic acid a) 3-Oxo-17α,20-epoxy-23,24-dinor-4-cholen-22-oic acid 0.4 ml of 30% $H_2O_2$ is added to a solution of 343 mg (1 mmol) of 3-oxo-23,24-dinor-4,17(20)-choladien-22-oic acid in a mixture containing 5 ml of pyridine and 0.4 ml of 0.5 M $Na_2WO_4$ solution at 60° C. The reaction is complete after about 15 minutes. The cooled reaction mixture is poured into 200 ml of 0.25% cold sodium sulfite solution, then the pH is adjusted to 3 with 6 M HCl solution. The resulting precipitate is filtered, washed with water and dried over $P_2O_5$ to give 340 mg of the named compound. Mp. 190°–195° C. (after recrystallization from acetone).

Analysis: calculated for $C_{22}H_{30}O_4$ (Mw=358.48); C: 73.71%; H: 8.44%,

Found: C: 73.50%; H: 8.51%; UV: λmax (ethanol): 241 nm;

IR (KBr, cm$^{-1}$): $\nu_{OH}$ 3200 (br); $\nu_{C=O}$ 1725, 1645; $\nu_{C=C}$ 1615;

$^1$H-NMR (DMSO-d$_6$,δ): 5.65 (d, J=1.7 Hz, 1 H-4), 1.51 (s, 3 H-21), 1.15 (s, 3 H-19), 0.90 (s, 3 H-18).

b) 3-Oxo-17α,20-epoxy-23,24-dinor -4-cholen-22oyl azide

77 μl (0.6 mmol) of butyl chloroformate is added to a solution of 195 mg (0.54 mmol) of 3-oxo-17α,20-epoxy-23,24-dinor-4-cholen-22-oic acid in a mixture of 5 ml of dichloromethane and 85 μl of triethylamine at −20° C. The solution is stirred for one hour during which time it gradually warms up to 15° C. Then a solution of 60 mg of sodium azide and 5 mg of tetrabutyl-ammonium bromide in 1 ml of water is added. After an additional period of half an hours at 20° C. the reaction mixture is diluted with dichloromethane and water. The organic phase is washed with water, dilute acetic acid and again water, then drived over anhydrous sodium sulfate and concentrated in vacuo. The solvent is changed to methanol from which the named compound crystallizes. Mp. 68°–70° C.

Analysis: calculated for $C_{22}H_{29}N_3O_3$ (Mw: 383.50); C: 68.90%; H: 7.62%; N: 10.96%, Found: C: 68.32%; H: 7.62%; N: 10.38.

UV: λ$_{max}$ (ethanol): 239 nm;

IR (KBr, cm$^{-1}$): $\nu_{azide}$ 2150; $\nu_{C=O}$ 1715, 1670; $\nu_{C=C}$ 1610;

$^1$H-NMR (CDCl$_3$, δ): 5.73 (d, J=1.7 Hz, 1 H-4), 1.63 (s, 3 H-21) 1.18 (s, H-19), 0.96 (s, 3 H-18).

c) 17α-Hydroxy-4-pregnene-3,20-dione

A boiling mixture of 3 ml of dimethylformamide and 3 ml of 20% acetic acid is added to 153 mg (0.4 mmol) of 3-oxo-17α,20-epoxy-23,24-dinor 4-cholen-22-oyl azide in 200 μl of chloroform. The reaction mixture is refluxed for 3 hours then concentrated in vacuo. The resulting crude product is purified by silicagel column chromatography. Elution with toluene-acetone (92:8) furnishes the named compound. Mp. 218°–221° C. [220°–222° C. accoridng to H. J. Ringold et al.: J. Am. Chem. Soc. 78, 816 (1956)].

Analysis: calculated for $C_{21}H_{30}O_3$ (Mw=330.47); C: 76.32%; H: 9.15%,

Found: C: 76.18%; H: 9.28%.

[α]$_D$:+94° (c=1, chloroform) (+95° according to literature cited above.

UV:λ$_{max}$ (ethanol): 240 nm;

IR (KBr, cm$^{-1}$):δ$_{OH}$ 3310 (br), $\nu_{C=O}$ 1705, 1660; $\nu_{C=C}$ 1610;

$^1$H-NMR (CDCl$_3$,δ): 5.74 (d, J=1.7 Hz, 1 H-4), 2.28 (s, 3 H-21), 1.19 (s, 3 H-19), 0.76 (s, 3 H-18).

EXAMPLE 2

Preparation of 17α-hydroxy-4,9(11) -pregnadiene-3,20-dione from 3-oxo-23,24 -dinor-4,9(11),17(20)-cholatrien 22-oic acid a) 3-Oxo-17,α,20-epoxy-23,24-dinor -4,9(11)-choladien-22-oic acid 10 ml of 30% $H_2O_2$ is added to a solution of 10.22 g (30 mmol) -of 3-oxo-23,24-dinor-4,9(11), 17(20) -cholatrien-22-oic acid in a mixture of 150 mol of pyridine and 10 ml of 0.5 M $Na_2WO_4$ solution at 60° C. The reaction is complete after about 15 minutes. The cooled reaction mixture is poured into 2 liters of 0.25% cold sodium sulfite solution, then the pH is adjusted to 3 with 6 M HCl solution. After standing for 2 hours the resulting precipitate is filtered, washed with water and dried over $P_2O_5$ to give 10.39 g of the named compound.

Mp. 202°–205° C. (after recrystallization from acetone).

Analysis: calculated for $C_{22}H_{28}O_4$ (Mw=356.47); C: 74.13%; H: 7.92%,

Found: C: 74.17%; H: 7.98%.

UV:λ$_{max}$ (ethanol): 240 nm;

IR (KBr, cm$^{-1}$): $\nu_{OH}$ 3320 (br); $\nu_{C=O}$ 1750, 1665; $\nu_{C=C}$ 1615.

$^1$H-NMR (DMSO-d$_6$,δ): 5.68 (d, J=1.7 Hz, 1 H-4), 5.46 (dd, J=5.8 and 1.8 Hz, 1 H-11), 1.51 (s, 3 H-21), 1.32 (s, 3 H-19), 0.85 (s, 3 H-18).

b) 3-Oxo-17α,20-epoxy-23,24-dinor -4,9(11)-choladien-22-oxy azide 1.55 ml (16 mmol) of ethyl chloroformate is added to a solution of 5.35 g (15 mmol) of 3-oxo-17α,20-epoxy-23,24-dinor -4,9(11)-choladien-22-oic acid in a mixture of 100 ml of dichloromethane and 2.1 ml of triethylamine at −20° C. The solution is stirred for 1 hour during which time it gradually warms up to 15° C. Then a solution of 1.46 g (22.5 mmol) of sodium azide and 50 mg of tetrabutyl-ammonium bromide in 15 ml of water is added. After an additional period of half an hour at 20° C. the reaction mixture is diluted with water and dichloromethane. The organic phase is washed with water, 5% sodium hydrogen carbonate solution and water, then dried over anhydrous sodium sulfate and concentrated cautiously in vacuo. The solvent is changed to acetone to give the crystalline named compound in a yield of 4.70 g (82%). The crystals loose nitrogen at 68°-69° C., then melt at 165°-170° C.

Analysis: calculated for $C_{22}H_{27}N_3O_3$ (381.48); C: 69.27%; H: 7.13%; N: 11.02%;

Found: C: 69.52%; H: 7.41%; N: 10.90%.

UV:$\lambda_{max}$ (ethanol): 238 nm;

IR (KBr, cm$^{-1}$):$\nu_{azide}$ 2140; $\nu_{C=O}$ 1705, 1670; $\nu_{C=C}$ 1615;

$^1$H-NMR (CDCl$_3$,δ): 5.76 (d, J=1.7 Hz, 1 H-4), 5.49 (dd, J=5.8 and 1.8 Hz, 1 H-11), 1.63 (s, 3 H-21), 1.35 (s, 3 H-19), 0.93 (s, 3 H-18).

c) 17α-Hydroxy-4,9(11)-pregnadiene 3,20-dione

A boiling mixture containing 30 ml of water, 6 ml of acetic acid, 15 ml of t-amyl alcohol and 10 ml of t-butyl alcohol is poured into a solution of 572 mg (1.5 mmol) of 3-oxo-17α,20-epoxy-23,24-dinor-4,9(11)-choladien -22-oyl azide in 0.5 ml of chloroform. The reaction mixture is refluxed for 4 hours then concentrated in vacuo to give 444 mg of crude named compound. The crude product obtaiend is purified by silicagel coloumn chromatography. Elution with toluene-acetone (92:8) furnishes the pure named compound.

Mp. 211°-215° C. [212°-217° C. according to H. Reimann et al.: J. Org. Chem. 26, 866 (1961)].

Analysis: calculated for $C_{21}H_{28}O_3$ (Mw: 328.45); C: 76.79%; H: 8.59% ,

Found: C: 76.79%; H: 8.80%.

[α]$_D$:+69.6° (c=0.8, chloroform) (+69° according to literature cited above);

UV:$\lambda_{max}$ (ethanol): 240nm;

IR (KBr, cm$^{-1}$); $\nu_{OH}$ 3355 (br), $\nu_{C=O}$ 1705, 1660; $\nu_{C=C}$ 1610;

$^1$H-NMR (CDCl$_3$δ): 5.77 (d, J=1.7 Hz, 1 H-4), 5.56 (dd, J=5.8 and 1.8 Hz, 1 H-11), 2.30 (s, 3 H-21), 1.34 (s, 3 H-19), 0.72 (s, 3 H-18).

EXAMPLE 3

Preparation of 17α-hydroxy-4,9(11)

-pregnadiene-3,20-dione from 3-oxo

-23,24-dinor-4,9(11),17(20)

-cholatrien-22-oic acid a) 3-Oxo-17α,20-epoxy-23,24

-dinor-4,9(11)-choladien-22-oic acid 341 mg (1 mmol) of 3-oxo -23,24-dinor-4,9(11),17(20) -cholatrien-22-oic acid is dissolved in a mixutre of 5 ml of pyridine and 0.5 ml of an aqueous solution of 17.3 mg of $(NH_4)_6MO_7O_{24}.4H_2O$ at 30° C., and 0.5 ml of 30% $H_2O_2$ is added. The reaction mixture is stirred for 30 minutes then poured into 100 ml of 2% cold hydrochloric acid solution. The solid material is filtered, wahsed with dilute HCl and water then dried over $P_2O_5$ to give 340 mg of the named compound. This product is spectroscopically and chromatographically identical with the product of Exmaple 2a.

b) 3-Oxo-17α,20-epoxy-23,24

-dinor-4,9(11)-choladien-22

-oic acid 1866 mg (5 mmol) of $H_2MoO_b.OP$ $(NMe_2)_3$ prepared by a method described in Ger. Offen. No. 1,815,998 is added in small portions to a solution of 1022 mg (3 mmol) of 3-oxo-23,24-dinor-4,9(11),17(20)-cholatrien-22-oic acid in 50 ml of t-butanol at 30° C. The reaction mixture is stirred for 45 minutes then poured into 500 ml of cold water. The pH of this slurry is adjusted to 3, the solid material is filtered, washed with water then dried over $P_2O_5$ to give 985 mg (92%) of the named compound. This product is spectroscopically and chromatographically identical with the product of Example 2a.

c) 17α-Hydroxy-4,9(11)

-pregnadiene-3,20-dione 1.3 ml of i-butyl chloroformate is added to a solution of 3.57 g (10 mmol) of 3-oxo-17α, 20-epoxy-23,24-dinor-4,9(11) -choladien-22-oic acid in a mixture of 70 mol of dichloromethane and 1.4 ml of triethylamine at −30° C. The solution is stirred for 0.5 hour during which time it gradually warms up to 5° C. A solution of 1.0 g (15.4 mmol) of sodium azide and 30 mg tetrabutyl ammonium bromide in 10 ml of water is added. After an additional period of half an hour at 20° C. the reaction mixture is diluted with dichloromethane and water. The organic phase is washed with water and dilute acetic acid then concentrated cautiously in vacuo until the azide starts to crystallize. To this solution a boiling mixture of 100 ml of ethanol, 50 ml of methanol and 100 ml of 10% acetic acid is added. The resulting reaction mixture is refluxed for 3 horus then concentrated in vacuo. This slurry is diluted with dichloromethane, washed with water, dried over sodium sulfate and evaporated furnishing 3.1 g of the desired compound which is spectroscopically and chromatographically identical with the product of Example 2c.

EXAMPLE 4

Preparation of i-butyloxycarbonyl 3-oxo-17α, 20-epoxy-23,24-dinor-4,9(11)

-choladien-22-oate

138 μl of i-butyl chloroformate are added to 357 mg (1 mmol) of 3-oxo -17α,20-epoxy-23,24-dinor-4,9(11) -choladien-22-oic acid in a mixture of 10 ml of dichloromethane and 150 μl of triethylamine at −20° C. The solution is stirred for one hour during which time it gradually warms up to 20° C. The reaction mixture is diluted with dichloromethane and water. The cold organic phase is washed with water, dilute sodium hydrogen carbonate and acetic acid solutions then water again, dried over anhydrous sodium sulfate and evaporated cautiously in vacuo to give 421 mg of the named compound as a colorless oil.

IR (neat, cm$^{-1}$); $\nu_{C=O}$ 1805, 1765, 1675; $\nu_{C=C}$ 1610;

$^1$H-NMR (CDCl$_3$,δ): 5.75 (d, J=1.7 Hz, 1 H-4), 5.48 (dd, J=5.8 and 1.8 Hz, 1 H-11), 4.07 (d, 2 H, OCH$_2$), 1.71 (s, 3 H-21), 1.37 (s, 3 H-19), 1.00 (d, 6 H, i-propyl), 0.69 (s, 3 H-18); $^{13}$C-NMR: 198.8 (C-3), 123.7 (C-4), 169.5 (C-5), 36.5 (C-8), 144.1 (C-9), 40.6 (C-10), 117.7 (C-11), 41.1 (C13), 49.8 (C14), 24.2 (C-15), 76.6 (C-17), 13.8 (C-18), 25.8 (C-19), 61.8 (C-20), 15.3 (C-21), 166.0

(C-22) and 6 further CH$_2$: 34.9, 33.9, 33.4, 32.4, 31.5, 28.8 and i-butyloxycarbonyl: 148.6, 75.6, 27.3, 18.4.

EXAMPLE 5 a) Preparation of 3-oxo-17α,20-epoxy -4,9(11)-pregnadienyl-20-isocyanate 76 mg (0.2 mmol) of 3-oxo-17α, 20-epoxy-23,24-dinor-4,9(11)-choladien -22-oyl azide are warmed in 500 μl of dideuterotetrachloroethane to 100° C. for 3 minutes then cooled to 10° C. The spectroscopic data of this solution are the following:

IR (neat, cm$^{-1}$): $\nu_{NCO}$ 2260; $\nu_{C=O}$ 1665; $\nu_{C=C}$ 1610;

$^1$H-NMR (δ): 5.64 (d, J=1.7 Hz, 1 H-4), 5.37 (dd, J=5.8 and 1.8 Hz, 1 H-11), 1.61 (s, 3 H-21), 1.25 (s, 3 H-19), 0.78 (s, 3 H-18);

$^{13}$C-NMR: 198.8 (C-3), 123.7 (C-4), 169.5 (C-5), 36.6 (C-8), 144.2 (C-9), 40.7 (C-10), 117.7 (C-11), 39.9 (C-13), 50.4 (C-14), 23.9 (C-15), 78.6 (C-17), 14.4 (C-18), 25.9 (C-19), 70.8 (C-20), 21.7 (C-21), 124.2 (isocyanate), and 6 further CH$_2$: 34.3, 34.0, 33.4, 32.5, 31.6, 30.4.

b) 17α-Hydroxy-4,9(11)-pregnadiene -3,20-dione

A boiling mixture containing 10 ml of i-propanol and 10 ml of 50% acetic acid is added to the solution of 3-oxo-17α,20-epoxy-4,9(11-pregnadienyl -20-isocyanate prepared in Example 5a. This reaction mixture is refluxed for 3 hours, then concentrated in vacuo and purified by the way described in Example 2c, furnishing the named compound which is spectroscopically and chromatographically identical with the product of Example 2c.

EXAMPLE 6

Preparation of 17α-hydroxy-1,4,9(11) -pregnatriene -3,20-dione from 3-oxo-23,24 -dinor-1,4,9(11),17(20) -cholatetraen-22-oic acid a) 3-Oxo-17α,20-epoxy-23,24 -dinor-1,4,9(11)-cholatrien-22-oic acid 3 ml of 30% H$_2$O$_2$ is added to a solution of 2.705 g (8 mmol) of 3-oxo -23,24-dinor-1,4,9(11),17(20) -cholatetraen-22-oic acid in a mixture of 50 ml of pyridine and 3 ml of 0.5 M Na$_2$WO$_4$ solution at 60° C. The reaction is complete after about 15 minutes. The cooled reaction mixture is poured into 500 ml of 0.25% cold sodium sulfite solution, then the pH is adjsuted to 3 with 6 M HCl solution. The resulting precipitate is filtered, washed with water and dried over P$_2$O$_5$ to give 2.70 g of the named compound. Mp. 193°-195° C. (after recrystallization from acetone).

Analysis: calculated for C$_{22}$H$_{26}$O$_4$ (354.45); C: 74.55%; H: 7.39%,
Found: C: 74.59%, H: 7.38%.
UV: λ$_{max}$ (ethanol): 240 nm;
IR (KBr, cm$^{-1}$): $\nu_{OH}$ 3325 (br); $\nu_{C=O}$ 1750, 1665; $\nu_{C=C}$ 1620;
$^1$H-NMR (DMSO-d$_6$,δ): 7.35 (1 H-1), 6.05 (1 H-2), 5.97 (1 H-4), (AMXm, J$_{1,2}$=10, J$_{2,4}$=2, J$_{1,4}$ ~0 Hz), 5.47 (dd, J=5.8 and 1.8 Hz, 1 H-11), 1.49 (s, 3 H-21), 1.34 (s, 3 H-19), 0.85 (s, 3 H-18).

3-Oxo-17α,20-epoxy-23,24 -dinor-1,4,9(11)-cholatrien -b 22-oyl azide

145 μl (1.1 mmol) of i-butyl chloroformate are added to 355 mg (1 mmol) of 3-oxo -17α,20-epoxy-23,24-dinor-1,4,9(11) -cholatrien-22-oic acid in a mixture of 10 ml of dichloromethane and 150 μl of triethylamine at −20° C. The solution is stirred for 1 hour and during this time it gradually warms up to 15° C. Then a solution of 250 mg · of sodium azide and 15 mg of tetrabutyl-ammonium bromide in 1.5 ml of water is added. After an additional period of half an hour at 20° C. the reaction mixture is diluted with dichloromethane and water. The organic phase is washed with water, dilute acetic acid and water, then dried over anhydrous sodium sulfate and concentrated cautiously in vacuo. The solvent is changed to acetone to give the crystalline named compound in a yield of 281 mg (74%). The crystals loose nitrogen at 62°-65° C. then melt at 154°-158° C.

Analysis: calculated for C$_{22}$H$_{25}$N$_3$O$_3$ (379.46); C: 69.64%; H: 6.64% ; N: 11.07%,
Found: C: 69.84%; H: 6.76%; N: 11.09;
UV: λ$_{max}$ (ethanol): 238 nm;
IR (KBr, cm$^{-1}$): $\nu_{azide}$ 2155; $\nu_{C=O}$ 1715, 1660; $\nu_{C=C}$ 1620, 1605;
$^1$H-NMR (CDCl$_3$, δ): 7.17 (1 H-1), 6.28 (1 H-2), 6.07 (1 H-4), (AMXm, J$_{1,2}$=10, J$_{2,4}$=1,7, J$_{1,4}$~0 Hz, 5.49 (dd, J=5.8 and 1.8 Hz, 1 H-11), 1.61 (s, 3 H-21), 1.42 (s, 3 H-19), 0.93 (s, 3 H-18).

c) 17α-Hydroxy-1,4,9(11)-pregnatriene -3,20-dione

145 μl (1.1 mmol) of i-butyl chloroformate are added to a solution of 355 mg (1 mmol) of 3-oxo-17α,20-epoxy-23,24-dinor -1,4,9 (11)-cholatrien-22-oic acid in a mixture of 15 ml of dichloromethane and 140 μl of triethylamine at −15° C. The solution is stirred for 1 hour and during this time it gradually warms up to 15° C. Then a solution of 150 mg of sodium azide and 15 mg of tetrabutyl ammonium bromide in 1.5 ml of water is added. After an additional period of half an hour at 20° C. the reaction mixture is diluted with dichloromethane and water. The organic phase is washed with water and dilute acetic acid then without drying concentrated cautiously in vacuo until the azide starts to crystallize. To this solution a boiling mixture of 10 ml of ethanol, 5 ml of methanol and 10 ml of 50% acetic acid is added. The resulting reaction mixture is refluxed for 3 hours, cooled and diluted with 100 ml of dichloromethane. The organic layer is washed with water, dried over anhydrous sodium sulfate and evaporated yielding 323 mg of crude product which is purified by silicagel colomn chromatography. Elution with tolueneacetone (92:8) furnishes the named compound. Mp. 228°-231° C. [226°-230° C., according to H. Reimann et al.: J. Org. Chem. 26, 866 (1961)].

Analysis: calculated for C$_{21}$H$_{26}$O$_3$ (326.43); C: 77.27%; H: 8.03%;
Found: C: 77.46%; H: 8.24%.
[α]$_D$: −21° (c=1, chloroform);
UV: λ$_{max}$ (ethanol): 240 nm;
IR (KBr, cm$^{-1}$): $\nu_{OH}$ 3350 (br); $\nu_{C=O}$ 1705, 1665; $\nu_{C=C}$ 1615;
$^1$H-NMR (CDCl$_3$, δ): 7.18 (1 H-1), 6.29 (1 H-2), 6.09 (1 H-4), (AMXm, J$_{1,2}$=10, J$_{2,4}$=1.8, J$_{1,4}$~0 Hz), 5.56

(dd, J=5.8 and 1.8 Hz, 1 H-11), 2.30 (s, 3 H-21), 1.42 (s, 3 H-19), 0.74 (s, 3 H-18).

EXAMPLE 7

Preparation of 3β,17α-dihydroxy-5-pregnen-20-one from 3β-hydroxy 23,24-dinor-5,17(20)-choladiene-22-oic acid a) 3β-Hydroxy-17α, 20-epoxy-23,24-dinor-5-cholen-22-oic acid 0.8 ml of 30% $H_2O_2$ is added to a solution of 518 mg (1.5 mmol) of 3-β-hydroxy-23,24-dinor-5,17(20)-choladien-22-oic acid in a mixture of 7 ml of pyridine and 0.4 ml of 0.5 M $Na_2WO_4$ solution at 60° C. The reaction is complete after about 15 minutes.

The cooled reaction mixture is poured into 100 ml of 2% cold HCl solution. The precipitate is filtered and washed with water and dried over $P_2O_5$ to give the named compound. Mp. 173°-175° C. (after recrystallization from methanol).

Analysis: calculated for $C_{22}H_{32}O_4$ (360.50); C: 73.30%; H: 8.95%;

Found: C: 73.18%; H: 9.01%.

IR (KBr, cm$^{-1}$); $\nu_{OH}$ 3440, 2620 (br); $\nu_{C=O}$ 1725;

$^1$H-NMR (DMSO-d$_6$, δ): 5.26 (d, $J_{6,7}$=4.6 Hz; 1 H-6), 3.38 (m, 1 H-3), 1.52 (s, 3 H-21), 0.94 (s, 3 H-19), 0.88 (s, 3 H-18).

b) 3β-Hydroxy-17α,20-epoxy-23,24-dinor-5-cholen-22oyl azide

135 μl (1.4 mmol) of ethyl chloroformate is added to a solution of 361 mg (1 mmol) of 3β-hydroxy-17α,20-epoxy-23,24-dinor-5-cholen-22-oic acid in a mixture of 10 ml of dichloromethane and 140 μl of triethylamine at −20° C. The solution is stirred for one hour durng which time it gradually warms up to 15° C. Then a solution of 200 mg of sodium azide and 15 mg of tetrabutyl-ammonium bromide in 1.5 ml of water is added. After an additional period of half an hour at 20° C. the reaction mixture is diluted with dichloromethane and water. The organic phase is washed with water, dilute acetic acid and again water, then dried over anhydrous sodium sulfate and concentrated in vacuo. The solvent is changed to methanol to give the crystalline named compound. Mp. 87°-88° C.

Analysis: calculated for $C_{22}H_{31}N_3O_3$ (385.51); C: 68.54%; H: 8.11%; N: 10.90%, Found: C: 68.24%; H: 8.16%; N: 10.66%.

IR (KBr, cm$^{-1}$): $\nu$OH 3360 (br); $\nu_{azide}$ 2140; $\nu_{C=O}$ 1705;

$^1$H-NMR (CDCl$_3$,δ): 5.32 (d, $J_{6,7}$=4.6 Hz, 1 H-6), 3.51 (m, 1 H-3), 1.62 (s, 3 H-21), 0.99 (s, 3 H-19), 0.91 (s, 3 H-18).

c) 3β,17α-Dihydroxy-5-prognen-20-one

A boiling mixture containing 3 ml of i-propanol and 3 ml of 25% acetic acid is added to a solution of 77 mg (0.2 mmol) of 3β-hydroxy-17α, 20-epoxy-23,24-dinor-5-cholen-22-oyl azide in 200 μl of chloroform. The reaction mixture is refluxed for 7 hours, then concentrated in vacuo. The crude product obtained is purified by silicagel coloumn chromatography. Elution with toluene-acetone (9:1) furnishes the named compound. Mp. 267°-271° C. [271°-273° C. according to P. Hegner at al.: Helv. Chim. Acta, 24, 828 (1941)].

Analysis: calculated for $C_{21}H_{32}O_3$ (332.48); C: 75.86%; H: 9.70%;

Found: C: 75.78%; H: 9.75%.

IR (KBr, cm$^{-1}$): $\nu_{OH}$ 3340 (br); $\nu_{C=O}$ 1710;

$^1$H-NMR (DMSO-d$_6$,δ): 5.27 (d, $J_{6,7}$=4.6, 1 H-6), 3.27 (m, 1 H-3), 2.09 (s, 3 H-21), 0.94 (s, 3 H-19), 0.50 (s, 3 H-18).

We claim:

1. A compound of the Formula (II)

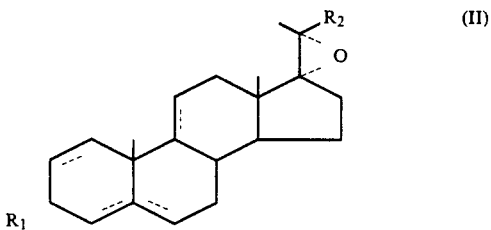

wherein

R$_1$ is a hydroxy or an oxo group;

R$_2$ is COOCOOC$_1$ $_{to}$ $_4$ alkyl, —CON$_3$ or —NCO group, and the dotted lines optionally represent one or more additional valence bonds, with the proviso that the dotted line in the 4-position and the dotted line in the 5-position cannot each simultaneously be an additional valence bond.

2. 3-Oxo-17α,20-epoxy-23,24-dinor -4-cholen-22-oyl azide as defined in claim 1.

3. 3-Oxo-17α,20-epoxy-23,24-dinor-4,9(11)-choladien-22-oyl azide as defined in claim 1.

4. 3-Oxo-17α,20-epoxy-23,24-dinor-1,4,9(11)-cholatrien-22-oyl azide as defined in claim 1.

5. 3β-Hydroxy-17α,20-epoxy -23,24-dinor-5-cholen-22oyl azide as defined in claim 1.

6. 3-Oxo-17α,20-epoxy-23,24-dinor-4,9(11-choladien-22-oic acid.

7. 3-Oxo-17α,20-epoxy-23,24-dinor-1,4,9(11)-cholatrien-22-oic acid.

* * * * *